(12) United States Patent
Keefer

(10) Patent No.: US 10,575,733 B2
(45) Date of Patent: *Mar. 3, 2020

(54) IMPLANT PLACEMENT SYSTEM AND METHOD WITH FEEDBACK

(71) Applicant: DEPUY SYNTHES PRODUCTS, INC., Raynham, MA (US)

(72) Inventor: Ryan C. Keefer, Warsaw, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/257,997

(22) Filed: Jan. 25, 2019

(65) Prior Publication Data
US 2019/0167108 A1    Jun. 6, 2019

Related U.S. Application Data

(63) Continuation of application No. 16/115,625, filed on Aug. 29, 2018, now Pat. No. 10,206,579, which is a continuation of application No. 14/870,202, filed on Sep. 30, 2015, now Pat. No. 10,085,645.

(51) Int. Cl.
| | |
|---|---|
| *A61B 5/00* | (2006.01) |
| *G16H 50/50* | (2018.01) |
| *A61B 17/16* | (2006.01) |
| *A61B 34/10* | (2016.01) |
| *G06F 19/00* | (2018.01) |
| *G16H 20/40* | (2018.01) |
| *A61B 5/055* | (2006.01) |
| *A61B 90/00* | (2016.01) |
| *A61B 90/30* | (2016.01) |

(52) U.S. Cl.
CPC .......... *A61B 5/0064* (2013.01); *A61B 5/0062* (2013.01); *A61B 5/4504* (2013.01); *A61B 5/4851* (2013.01); *A61B 17/1666* (2013.01); *A61B 34/10* (2016.02); *G06F 19/00* (2013.01); *G16H 20/40* (2018.01); *G16H 50/50* (2018.01); *A61B 5/004* (2013.01); *A61B 5/055* (2013.01); *A61B 2034/101* (2016.02); *A61B 2034/102* (2016.02); *A61B 2034/105* (2016.02); *A61B 2090/309* (2016.02); *A61B 2090/373* (2016.02)

(58) Field of Classification Search
CPC ..... A61B 34/10; A61B 5/0062; A61B 5/4504; A61B 5/4851; A61B 17/1666; G16H 20/40; G16H 50/50; G06F 19/00
See application file for complete search history.

(56) References Cited

U.S. PATENT DOCUMENTS

| | | | |
|---|---|---|---|
| 7,525,309 B2 | 4/2009 | Sherman et al. | |
| 7,615,055 B2 | 11/2009 | DiSilvestro | |
| 7,815,644 B2 * | 10/2010 | Masini | A61B 90/36 600/414 |
| 7,885,701 B2 | 2/2011 | DiSilvestro et al. | |
| 7,894,872 B2 | 2/2011 | Sherman | |

(Continued)

*Primary Examiner* — Edward Park
(74) *Attorney, Agent, or Firm* — Barnes & Thornburg LLP

(57) ABSTRACT

Methods for performing orthopaedic surgical procedures including generating scan data from the intra-operatives scans and comparing the scan data to a surgical plan are disclosed. The scan data and other feedback data are used to validate the position and orientation of orthopaedic prosthetic component implanted in a body of the patient.

20 Claims, 9 Drawing Sheets

(56) References Cited

U.S. PATENT DOCUMENTS

| | | | |
|---|---|---|---|
| 8,068,648 B2 | 11/2011 | DiSilvestro et al. | |
| 8,148,978 B2 | 4/2012 | Sherman et al. | |
| 8,265,949 B2 | 9/2012 | Haddad | |
| 8,357,165 B2 | 1/2013 | Grant et al. | |
| 8,394,104 B2 | 3/2013 | DiSilvestro | |
| 8,521,255 B2 | 8/2013 | DiSilvestro et al. | |
| 8,551,023 B2 | 10/2013 | Sherman et al. | |
| 8,556,830 B2 | 10/2013 | Sherman et al. | |
| 8,597,210 B2 | 12/2013 | Sherman et al. | |
| 8,608,745 B2 | 12/2013 | Guzman et al. | |
| 8,635,082 B2 | 1/2014 | Woods et al. | |
| 8,721,568 B2 | 5/2014 | Rock et al. | |
| 8,734,454 B2 | 5/2014 | DiSilvestro | |
| 8,740,817 B2 | 6/2014 | Sherman et al. | |
| 8,862,200 B2 | 10/2014 | Sherman et al. | |
| 10,085,645 B2 | 10/2018 | Keefer et al. | |
| 10,206,579 B2 | 2/2019 | Keefer | |
| 2011/0092858 A1* | 4/2011 | Burger | A61B 34/10 600/587 |
| 2016/0100958 A1* | 4/2016 | Behzadi | A61B 17/3468 606/91 |
| 2017/0086674 A1 | 3/2017 | Keefer | |

* cited by examiner

IMPLANT PLACEMENT SYSTEM AND METHOD WITH FEEDBACK

This application is a continuation application of and claims priority to U.S. patent application Ser. No. 16/115,625 filed Aug. 29, 2018, which is a continuation application of U.S. patent application Ser. No. 14/870,202, now U.S. Pat. No. 10,085,645, filed Sep. 30, 2015, each of which is expressly incorporated herein by reference.

TECHNICAL FIELD

The present disclosure relates generally to methods for performing orthopaedic surgical procedures and, more particularly, to methods that use intra-operative scans made using a hand-held device.

BACKGROUND

Joint arthroplasty is a well-known surgical procedure by which a diseased and/or damaged natural joint is replaced by a prosthetic joint. For example, in a hip arthroplasty surgical procedure, a patient's natural hip ball and socket joint is partially or totally replaced by a prosthetic hip joint. A typical prosthetic hip joint includes an acetabular prosthetic component and a femoral head prosthetic component. An acetabular prosthetic component generally includes an outer shell configured to engage the acetabulum of the patient and an inner bearing or liner coupled to the shell and configured to engage the femoral head. The femoral head prosthetic component and inner liner of the acetabular component form a ball and socket joint that approximates the natural hip joint.

To facilitate the replacement of the natural joint with a prosthetic hip joint, orthopaedic surgeons may use a variety of orthopaedic surgical methods such as, for example, trialing, to determine if an orthopaedic implant is positioned correctly in the patient.

SUMMARY

According to one aspect of the disclosure, a method of performing an orthopaedic surgical procedure on a patient is disclosed. The method includes positioning the patient on a surgical table in an operating room and making an incision in the patient's tissue to expose a bone of the patient. A hand-held device is used to obtain a first scan, the first scan including a position and an orientation of the bone in the operating room. The hand-held device transmits the first scan to a computing device. A member of the surgical team operates the computing device to compare the position and the orientation of the bone included in the first scan to a surgical plan including a planned position and a planned orientation of the patient's bone and to generate an adjusted planned position and an adjusted planned orientation of an orthopaedic prosthetic component in the patient's bone based on the position and the orientation of the bone included in the first scan. An orthopaedic prosthetic component is implanted in the bone of the patient. A second scan is obtained with the hand-held device, the second scan including a position and an orientation of the orthopaedic prosthetic component in the bone. The hand-held device transmits the second scan to the computing device. A member of the surgical team operates the computing device to confirm that the position and the orientation of the orthopaedic prosthetic component included in the second scan matches the adjusted planned position and the adjusted planned orientation of the orthopaedic prosthetic component.

The first scan may further comprise positioning an optical detector of the hand-held device inside of the incision formed in the patient's tissue, and performing the first scan with the hand-held device.

The hand-held device may further comprise an optical detector positioned on the hand-held device, the optical detector being configured to detect electromagnetic radiation reflected from a surface of interest on the patient. The hand-held device may be a white light scanner configured to determine one or more locations of a surface of interest on the patient by detecting one or more characteristics of white light reflected from the surface of interest. The hand-held device may be a laser scanner that includes one or more optical detectors configured to determine one or more locations on a surface of interest on the patient by detecting one or more characteristics of laser light reflected from the surface of interest.

When obtaining scans using the hand-held device the patient is not moved to a new location and the position of the patient relative to a reference plane is not modified.

Operating the computing device may further comprises operating the computing device to display a comparison of the position and the orientation of the bone included in the first scan to the surgical plan that includes the planned position and the planned orientation of the patient's bone. Operating the computing device may also further comprise operating the computing device to display a comparison of the position and orientation of the orthopaedic prosthetic component included in the second scan to the surgical plan that includes the planned component position and planned component orientation of the orthopaedic prosthetic component in the patient's bone.

The orthopaedic surgical procedure may further include positioning an orthopaedic trialing component in the bone of the patient. The hand-held device is used to obtain a third scan, the third scan including a first position and a first orientation of the orthopaedic trialing component. The hand-held device transmits the third scan to the computing device. A member of the surgical team operates the computing device to determine trialing feedback data by comparing the first position and the first orientation of the orthopaedic trialing component included in the third scan to the surgical plan that includes a planned component position and a planned component orientation of the orthopaedic prosthetic component.

The orthopaedic surgical procedure may further include adjusting the orthopaedic trialing component to be in a second position and a second orientation in the bone of the patient based on the trialing feedback data. The hand-held device is used to obtain a fourth scan, the fourth scan including data related to the second position and the second orientation of the orthopaedic trialing component. A member of the surgical team operates the computing device to determine additional trialing feedback data by comparing the second position and the second orientation of the orthopaedic trialing component included in the fourth scan to the surgical plan.

The orthopaedic surgical procedure may yet further include selecting a different orthopaedic trialing component based on the trialing feedback data and positioning the different orthopaedic trialing component in the bone of the patient. The hand-held device is used to obtain a fifth scan, the fifth scan including a position and an orientation of the different orthopaedic trialing component. The hand-held device transmits the fifth scan from the hand-held device to the computing device. A member of the surgical team operates the computing device to compare the position and orientation of the different orthopaedic trialing component included in the fifth scan to the surgical plan.

In some embodiments, the hand-held device may transmit each of the scans to the computing device wirelessly.

According to another aspect, a method of performing an orthopaedic surgical procedure on a patient includes positioning the patient on a surgical table in an operating room and making an incision in the patient's tissue to expose a bone of the patient. A hand-held device is used to obtain a first scan, the first scan including a position and an orientation of the bone in the operating room, and transmits the first scan to a computing device. A member of the surgical team operates the computing device to compare the position and the orientation of the bone included in the first scan to a surgical plan including a planned position and a planned orientation of the patient's bone and to generate an adjusted planned position and an adjusted planned orientation of an orthopaedic prosthetic component in the patient's bone based on the position and the orientation of the bone included in the first scan. An orthopaedic trialing component is positioned in the bone of the patient based on the adjusted planned position and the adjusted planned orientation. The hand-held device is used to obtain a second scan, the second scan including a first position and a first orientation of the orthopaedic trialing component, and transmit the second scan to the computing device. A member of the surgical team operates the computing device to determine trialing feedback data by comparing the first position and the first orientation of the orthopaedic trialing component included in the second scan to the surgical plan that includes a planned component position and a planned component orientation of the orthopaedic prosthetic component.

The orthopaedic surgical procedure may further include adjusting the orthopaedic trialing component to be in a second position and a second orientation in the bone of the patient based on the trialing feedback data. The hand-held device is used to obtain a third scan, the third scan including data related to the second position and the second orientation of the orthopaedic trialing component and transmitting the third scan from the hand-held device to the computing device. A member of the surgical team operating the computing device to compare the second position and the second orientation of the orthopaedic trialing component included in the third scan to the surgical plan.

The orthopaedic surgical procedure may further include selecting a different orthopaedic trialing component based on the trialing feedback data, and positioning the different orthopaedic trialing component in the bone of the patient. The hand-held device being used to obtain a fourth scan, the fourth scan including a position and an orientation of the different orthopaedic trialing component, and transmitting the fourth scan from the hand-held device to the computing device. A member of the surgical team operating the computing device to determining additional trialing feedback data by comparing the position and orientation of the different orthopaedic trialing component included in the fourth scan to the surgical plan.

In some embodiments, the orthopaedic trialing component is positioned in the bone of the patient prior to implanting the orthopaedic prosthetic component in the bone of the patient. In such an embodiment, the orthopaedic prosthetic component is positioned in the bone of the patient based on the trialing feedback data.

The orthopaedic surgical procedure may include selecting a size of orthopaedic trialing component based on the position and the orientation of the bone included in the first scan, the size of the orthopaedic trialing component being different than the size of the orthopaedic trialing component specified in the surgical plan.

In some embodiments, the hand-held device may transmit each of the scans to the computing device wirelessly.

According to another aspect, a method of performing an orthopaedic surgical procedure on a patient includes positioning the patient on a surgical table in an operating room, making an incision in the patient's tissue to expose a bone of the patient, and positioning an orthopaedic trialing component in the bone of the patient based on a surgical plan that includes a planned position, and a planned orientation. A hand-held device is used to obtain a first scan, the first scan including a first position and a first orientation of the orthopaedic trialing component, and to transmit the first scan from the hand-held device to a computing device. A member of the surgical team operates the computing device to determine trialing feedback data by comparing the first position and the first orientation of the orthopaedic trialing component included in the first scan to the surgical plan, and to implant an orthopaedic prosthetic component in the bone of the patient. The hand-held device is used to obtain a second scan, the second scan including a component position and a component orientation of the orthopaedic prosthetic component in the bone, and to transmit the second scan from the hand-held device to the computing device. A member of the surgical team operates the computing device to confirm that the component position and the component orientation of the orthopaedic prosthetic component included in the second scan matches the planned position and the planned orientation of the orthopaedic prosthetic component.

The orthopaedic surgical procedure may further include having a member of the surgical team operating the computing device to determine an adjusted position and an adjusted orientation based on the trialing feedback data, implanting the orthopaedic prosthetic component in the bone of the patient in the adjusted position and in the adjusted orientation, and operating the computing device to confirm that the component position and the component orientation of the orthopaedic prosthetic component included in the second scan matches the adjusted position and the adjusted orientation.

In some embodiments, the adjusted position determined from the trialing feedback data is different than the planned position included in the surgical plan and the adjusted orientation determined from the trialing feedback data is different than the planned orientation included in the surgical plan.

In some embodiments, the surgical plan further includes a planned prosthetic size. In such embodiments, the orthopaedic surgical procedure may further include selecting the orthopaedic trialing component based on the planned prosthetic size included in the surgical plan. A member of the surgical team may operate the computing device to compare the first position and the first orientation of the orthopaedic trialing component included in the first scan to determine a new prosthetic size, and select the orthopaedic prosthetic component to implant in the bone of the patient based on the new prosthetic size.

In some embodiments, the hand-held device may transmit each of the scans to the computing device wirelessly.

According to another aspect, a method of performing an orthopaedic surgery on a patient includes positioning the patient on a surgical table in an operating room, making an incision in the patient's tissue to expose a bone of the patient, obtaining a first scan with a hand-held device, the first scan including a position and an orientation of the bone in the operating room, transmitting the first scan from the hand-held device to a computing device, and operating the computing device to (i) compare the position and the orientation of the bone included in the first scan to a surgical plan including a planned position and a planned orientation of the patient's bone and (ii) generate an adjusted planned position and an adjusted planned orientation of an orthopaedic prosthetic component in the patient's bone based on the position and the orientation of the bone included in the first scan.

BRIEF DESCRIPTION OF THE DRAWINGS

The detailed description particularly refers to the following figures, in which.

DETAILED DESCRIPTION OF THE DRAWINGS

Figure 1:
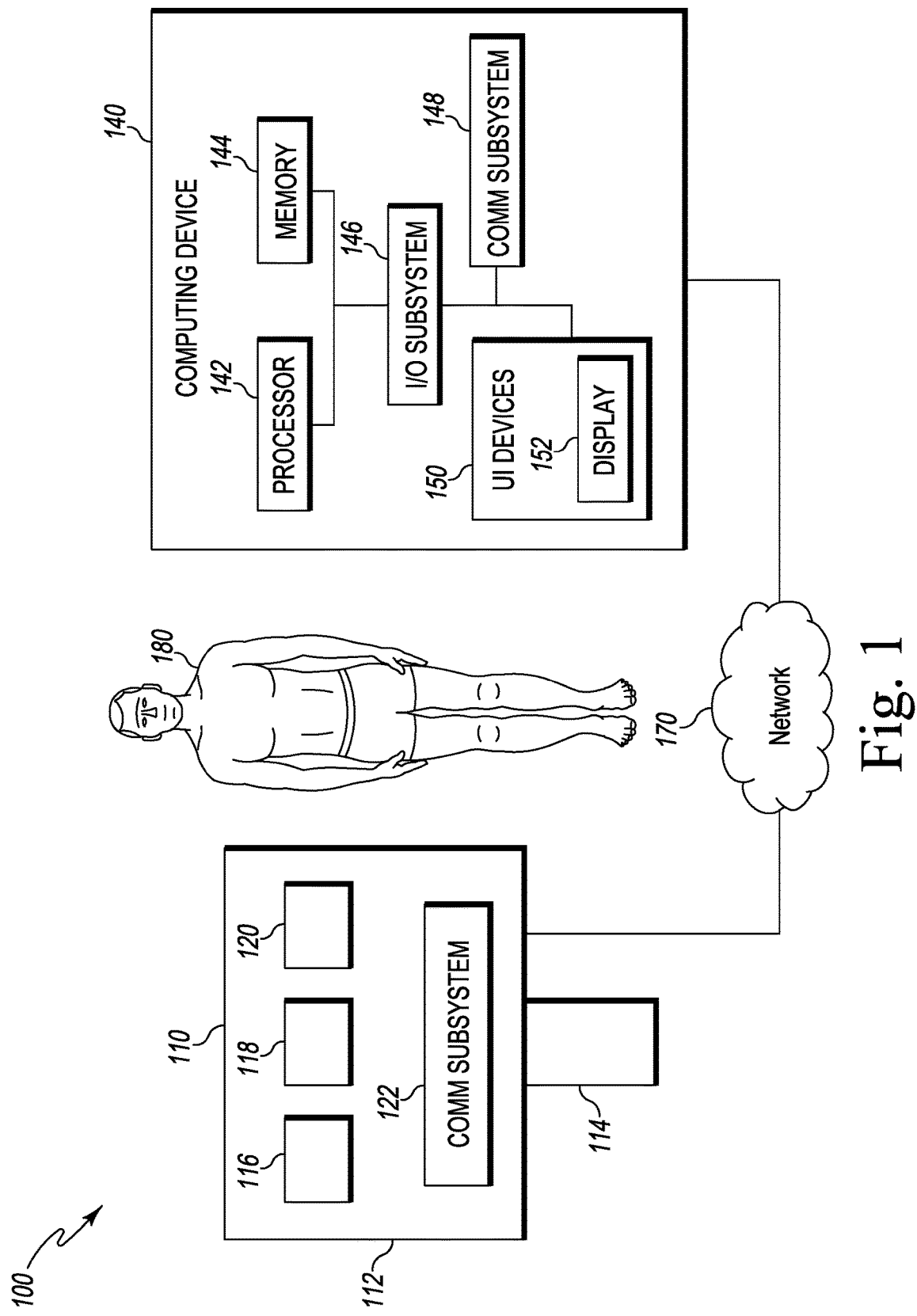
FIG. 1 is a simplified block diagram of one embodiment of a system for performing intra-operative scans on a patient during an orthopaedic surgical procedure.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring to FIG. 1, a surgical feedback system 100 is configured to perform one or more intra-operative scans. The surgical feedback system 100 comprises a hand-held device 110 connected to a computing device 140 via a network 170. The hand-held device 110 is configured to generate scan data of a surface of interest on a patient 180 during an orthopaedic surgical procedure. The surface of interest on the patient 180 includes an exposed bone 810 of the patient 180 and a surgical region around the exposed bone 810 (see FIG. 10). From the scan data generated by the hand-held device 110, the surgical feedback system 100 may be configured to identify an orientation of the patient's bone 810, compare a current position of the patient's bone 810 to a planned position included in a surgical plan (see FIGS. 8 and 9), determine an implantation angle of an orthopaedic surgical component, and/or determine a position and an orientation of the orthopaedic surgical component implanted in the patient 180 (see FIG. 10).

The hand-held device 110 includes a housing 112 and a handle 114 configured to be graspable by a user of the hand-held device 110. The hand-held device 110 also includes one or more optical devices 116, 118, 120 and a communication subsystem 122. In the illustrative embodiment, the hand-held device 110 is a three-dimensional white light scanner. The one or more optical devices 116, 118, 120 are configured to scan the surface of a patient's bone 810 to generate scan data of the surface using electromagnetic radiation. The optical devices 116, 118, 120 may include at least one emitter 116, at least two detectors 118, 120. The emitter(s) 116 are configured to illuminate one or more points on the surface of interest with electromagnetic radiation (i.e., light). The detectors 118, 120 are configured to detect the electromagnetic radiation reflected by the surface of interest. The emitter(s) 116 may be embodied as a laser, a light emitting diode, an infrared emitter, or any other type of electromagnetic radiation source. The at least two detectors 118, 120 may be embodied as a camera, a charge-coupled device (CCD), phototransistor, or another type of sensor configured to detect electromagnetic radiation. In the illustrative embodiment of FIG. 1, the hand-held device 110 includes one emitter 116 and two detectors 118, 120, however, the hand-held device 110 may include any number of emitters and optical detectors to perform the functions described herein.

In the illustrative embodiment of FIG. 1, the hand-held device 110 is a white light scanner configured to determine one or more locations on the surface of interest on the patient 180 by illuminating the surface of interest with white light and determining one or more locations on the surface of interest based on white light reflected from the surface of interest. Specifically, an emitter 116 of the white light scanner illuminates one or more points on the surface of interest with white light comprises electromagnetic radiation across a range of frequencies. The detectors 118, 120 receive the white light reflected from the surface of interest. One or more path length delays of the white light are determined. Based on the path length delays at different frequencies of electromagnetic radiation (e.g., visible light), one or more locations on the surface of interest are determined.

In another embodiment, the hand-held device 110 may be a laser scanner configured to illuminate the surface of interest with light emitted from a laser and determine one or more locations on the surface of interest by measuring a time-delay between emission of the light and detection of the light and the shape of the light when it is detected. Based on the time-delay and the shape of the light received by the one or more optical detectors, one or more locations on the surface of interest may be determined. In some embodiments, the time-delays and the shape of the light detected by different optical detectors is compared when determine one or more positions on the surface of interest.

The communication subsystem 122 of the hand-held device 110 connects the hand-held device 110 to one or more other devices, including the computing device 140. The communication subsystem 122 is configured to connect the hand-held device 110 to one or more networks 170, e.g., a local area network, wide area network, personal cloud, enterprise cloud, public cloud, a Near Field Communication (NFC) connection, and/or the Internet, for example. Accordingly, the communication subsystem 122 may include one or more short and/or long range wired or wireless (including optical) network interface software, firmware, or hardware, for example, as may be needed pursuant to the specifications and/or design of the particular embodiment of the system 100. The communication subsystem 122 may be configured to establish communication using many types of networks 170 and/or network protocols, such as, for example, WiFi, a BLUETOOTH®, or Ethernet communication protocols.

The illustrative computing device 140 is configured to process the scan data generated by the hand-held device 110 and generate feedback data to be used during an orthopaedic surgical procedure. As described in more detail below, feedback data may include bone alignment data, trialing feedback data, or implant feedback data. The computing device 140 includes at least one processor 142 (e.g. a microprocessor, microcontroller, digital signal processor, etc.), memory 144, and an input/output (I/O) subsystem 146. In operation, processor 142 fetches and executes instructions and information, and generates and transfers information to and from other resources coupled to or in data communication with the processor 142. The computing device 140 may be embodied as any type of computing device capable of performing the functions described herein, such as a personal computer (e.g., desktop, laptop, tablet, smart phone, mobile device, body-mounted device, wearable device, etc.), a server, an enterprise computer system, a network of computers, a combination of computers and other electronic devices, or other electronic devices. Although not specifically shown, it should be understood that the I/O subsystem 146 typically includes, among other things, an I/O controller, a memory controller, and one or more I/O ports. The processor 142 and the I/O subsystem 146 are connected to the memory 144. The memory 144 may be embodied as any type of suitable computer memory device (e.g., volatile memory such as various forms of random access memory). In some embodiments, the memory 144 is RAM and may temporarily store instructions and data retrieved from slower storage devices as needed for current operations, from which they can be more quickly read and processed by the processor 142 or other hardware devices. The I/O subsystem 146 is communicatively coupled to a number of hardware and/or software components, including a communication subsystem 148 and one or more user interface devices 150. It should be understood that each of the foregoing components and/or systems may be integrated with the computing device 140 or may be a separate component or system that is in communication with the I/O subsystem 146 (e.g., over a network 170 or a bus connection).

The communication subsystem 148 is configured to connect the computing device 140 to one or more other devices, for example, the hand-held device 110. The communication subsystem 148 is similarly embodied as the communication subsystem 122 and includes the same functionality described above. As such, a full description of the communication subsystem 148 is not repeated here.

The one or more user interface devices 150 are configured to allow the user to provide inputs to the computing device 140 and receive outputs from the computing device 140. The illustrative embodiment of the one or more user interface devices 150 includes a display 152 configured to display pre-operative data and intra-operative (e.g., feedback data) data to the user. In other embodiments the one or more user interface devices may also include a keyboard, a mouse, a touchpad, a touch screen, one or more speakers, or any other type of input/output device.

Figure 2:
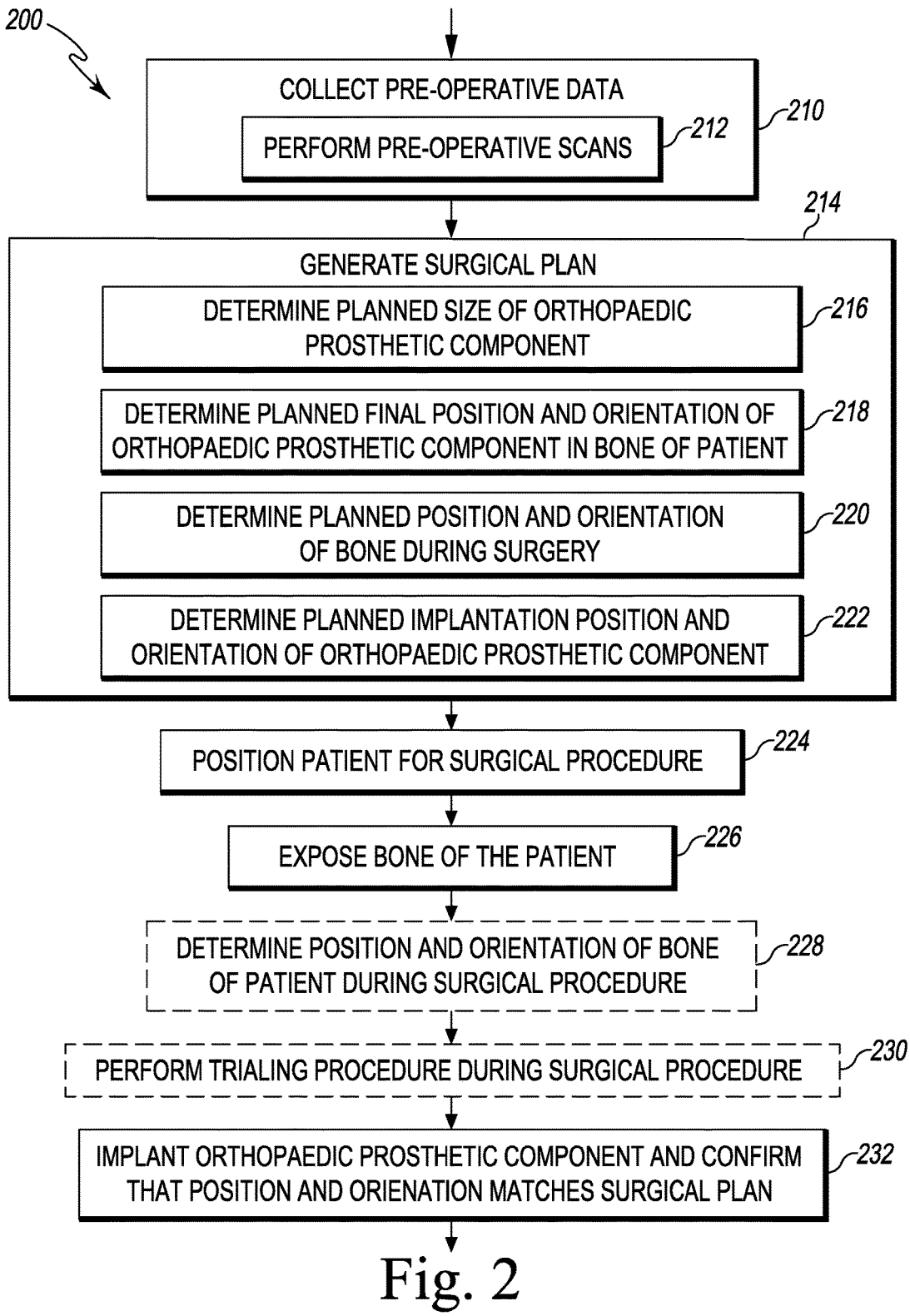
FIG. 2 is a simplified flow diagram of an embodiment of a method for performing the orthopaedic surgical procedure of FIG. 1.

Referring to FIG. 2, a method 200 for using the surgical feedback system 100 during an orthopaedic surgical procedure is shown. In the illustrative embodiment, the orthopaedic surgical procedure is a joint arthroplasty procedure, such as a hip arthroplasty procedure. In other embodiments, the orthopaedic surgical procedure may be a knee arthroplasty procedure.

At block 210, pre-operative data for the patient 180 is collected. As used in this application, "pre-operative data" refers to any data that is collected prior to performing an orthopaedic surgical procedure and may be used to generate a surgical plan for the orthopaedic surgical procedure. An example of pre-operative data includes pre-operative scan data generated by performing one or more pre-operative scans (at block 212). The pre-operative scan data may include data generated by a camera, an x-ray scanner, a CT scanner, an MRI, scanner or data generated by other types of imaging devices. Other examples of pre-operative scan data include one or more pre-operative images, such as photographs, x-ray images, images generated by a CT scanner, images generated by an MRI scanner, other images generated by other types of imaging devices, and/or surgeon preferences.

At block 214, a surgeon, or another member of the surgical team, generates a surgical plan for the orthopaedic surgical procedure based on the pre-operative data (including the pre-operative scan data). In some embodiments, the images generated from the pre-operative scans (see FIG. 10) are used to generate a three-dimensional model of the surface of interest on the patient's bone 810.

As used in this application, a "surgical plan" is a set of surgical parameters for performing the orthopaedic surgical procedure and includes specifications for placement of the orthopaedic prosthetic component and how the orthopaedic prosthetic component should function in the patient 180. For example, a surgical plan may include a planned type of the orthopaedic prosthetic component, a planned size of the orthopaedic prosthetic component, a planned final position of the orthopaedic prosthetic component, a planned final orientation of the orthopaedic prosthetic component (see FIG. 10), a planned position of the patient's bone 810 during the orthopaedic surgical procedure (see FIG. 8), a planned orientation of the patient's bone 810 during the orthopaedic surgical procedure, a planned implantation angle, and/or a plan for a trialing process.

Generating the surgical plan may include determining a number of different surgical parameters, including parameters about an orthopaedic prosthetic component. The orthopaedic prosthetic component is an artificial device that may be implanted in the body to replace a missing body part. For example, an acetabular cup prosthesis (see, for example, orthopaedic component 1010 in FIG. 10) may be implanted in a coxal bone 810 of the patient 180 in place of the patient's acetabulum. Orthopaedic components 1010 may include orthopaedic prosthetic components, which are intended to be implanted in the body, or orthopaedic trialing components, which are intended to only be used during an orthopaedic surgical procedure. At block 216, a member of the surgical team determines a planned size of the orthopaedic prosthetic component based on the pre-operative data. The planned size of the orthopaedic prosthetic component may also include a planned type of the orthopaedic prosthetic component. For example, if a hip arthroplasty is being performed, a planned size of an acetabular cup prosthetic component and/or a femoral stem prosthetic component may be chosen. At block 218, based on the pre-operative data, a member of the surgical team selects a planned final position and a planned final orientation of the orthopaedic prosthetic component in the bone 810.

At block 220, a member of the surgical team determines a planned position and a planned orientation of the bone 810 of the patient 180 during surgery based on the pre-operative data. At block 222, a planned implantation angle of the orthopaedic prosthetic component is determined based on the planned final position and orientation of the orthopaedic prosthetic component and the planned position and orientation of the patient's bone 810 during the orthopaedic surgical procedure. The planned implantation angle is configured to provide a reference angle to a surgeon to ensure that the orthopaedic prosthetic component is implanted correctly given a particular position and orientation of the patient 180.

During the orthopaedic surgical procedure, at block 224, the patient 180 is positioned on a surgical table in an operating room for the orthopaedic surgical procedure. At block 226, a surgeon makes an incision in the patient's tissue to expose a bone of the patient 180. In the case of a hip arthroplasty procedure, the exposed bone may be a coxal or pelvic bone of the patient 180 (e.g., bone 810) or a proximal end of a femur. In the case of a knee arthroplasty procedure, the exposed bone may be a distal end of the femur or a proximal end of a tibia.

Figure 3:
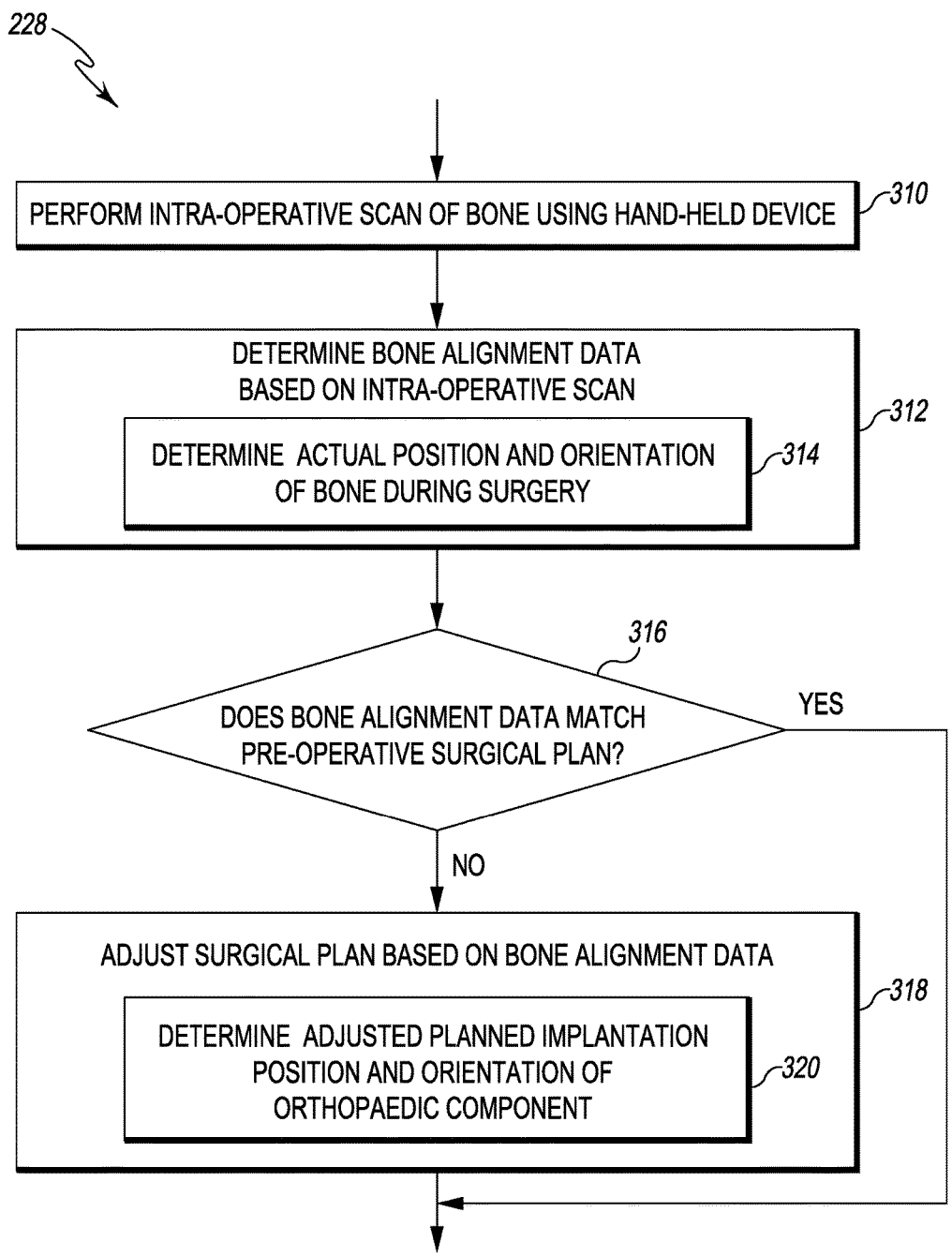
FIG. 3 is a simplified flow diagram for determining the position and orientation of the bone of the patient during the orthopaedic surgical procedure.

At block 228, during the orthopaedic surgical procedure, a position and an orientation of the patient's bone 810 may optionally be determined using one or more intra-operative scans and the pre-operative data. A more detailed description of block 228 is provided below and is shown in FIG. 3. In some embodiments, the only intra-operative scan performed during an orthopaedic surgical procedure is a bone alignment scan. The bone alignment scan configured to determine the tilt of a patient's coxal bone.

Figure 4:
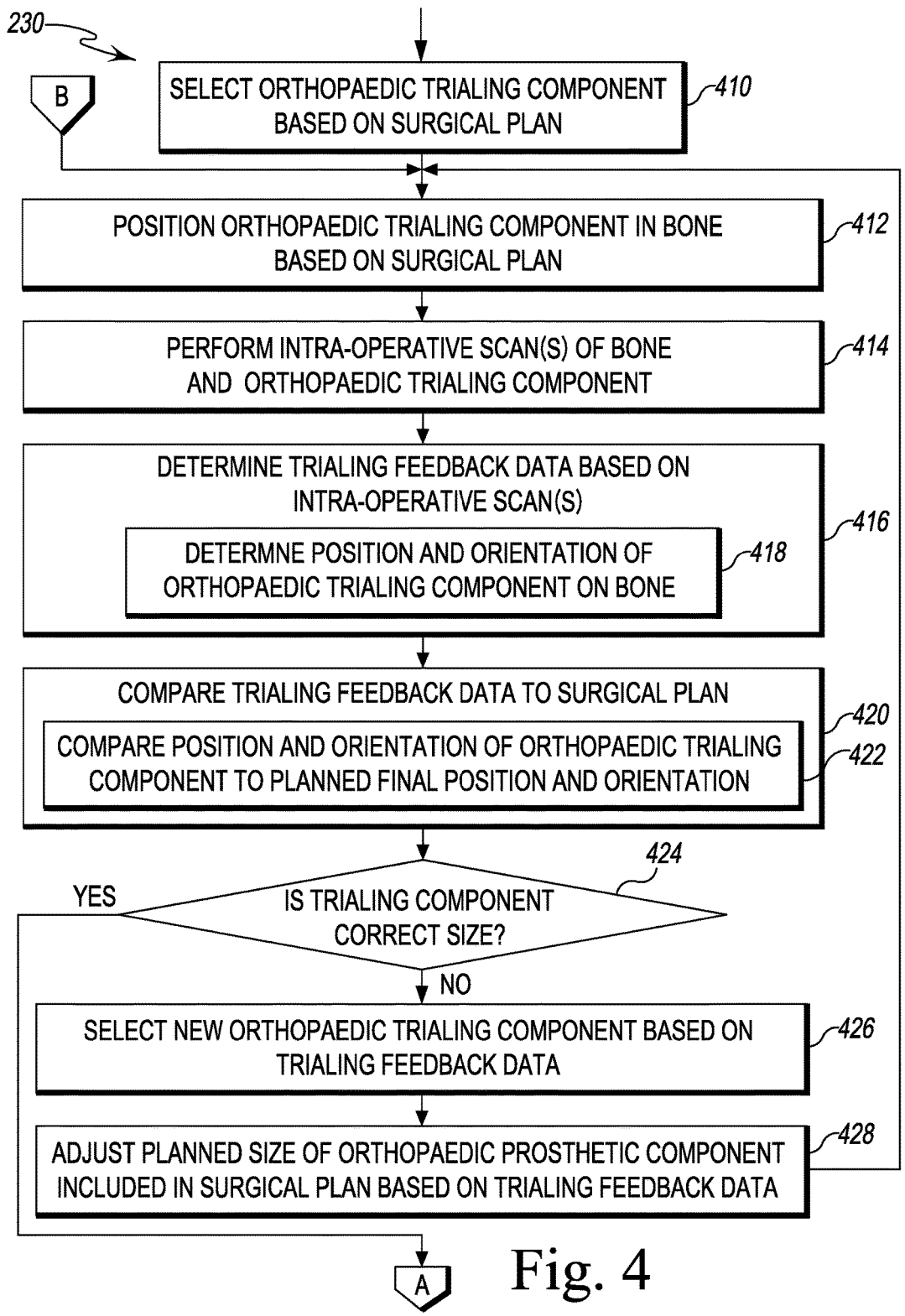
FIGS. 4-5 are a simplified flow diagram for performing a trialing procedure during the orthopaedic surgical procedure.
Figure 5:
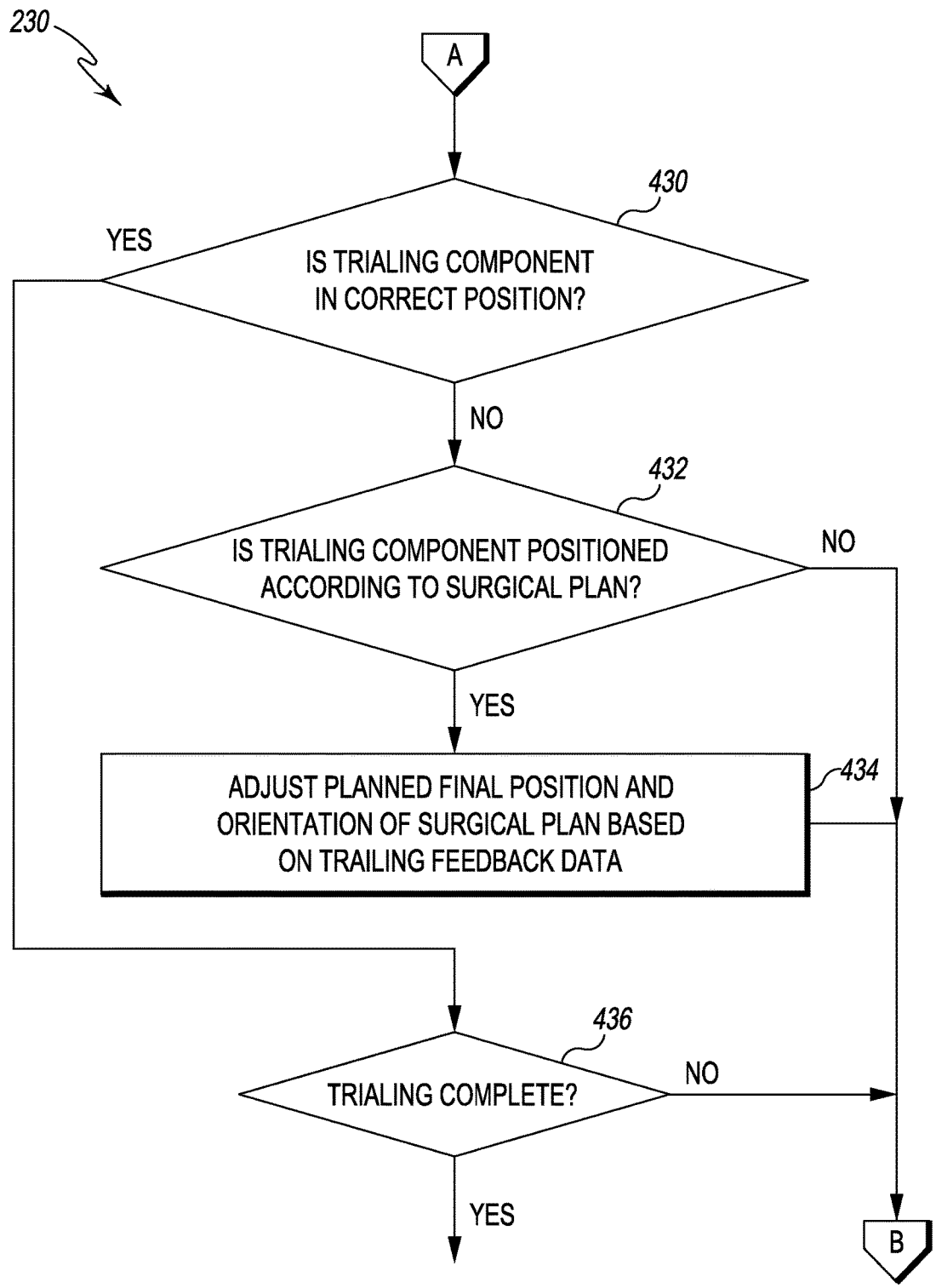

At block 230, during the orthopaedic surgical procedure, a trialing procedure may optionally be performed using one or more intra-operative scans and the pre-operative data. A more detailed description of block 230 is provided below and is shown in FIGS. 4-5.

Figure 6:
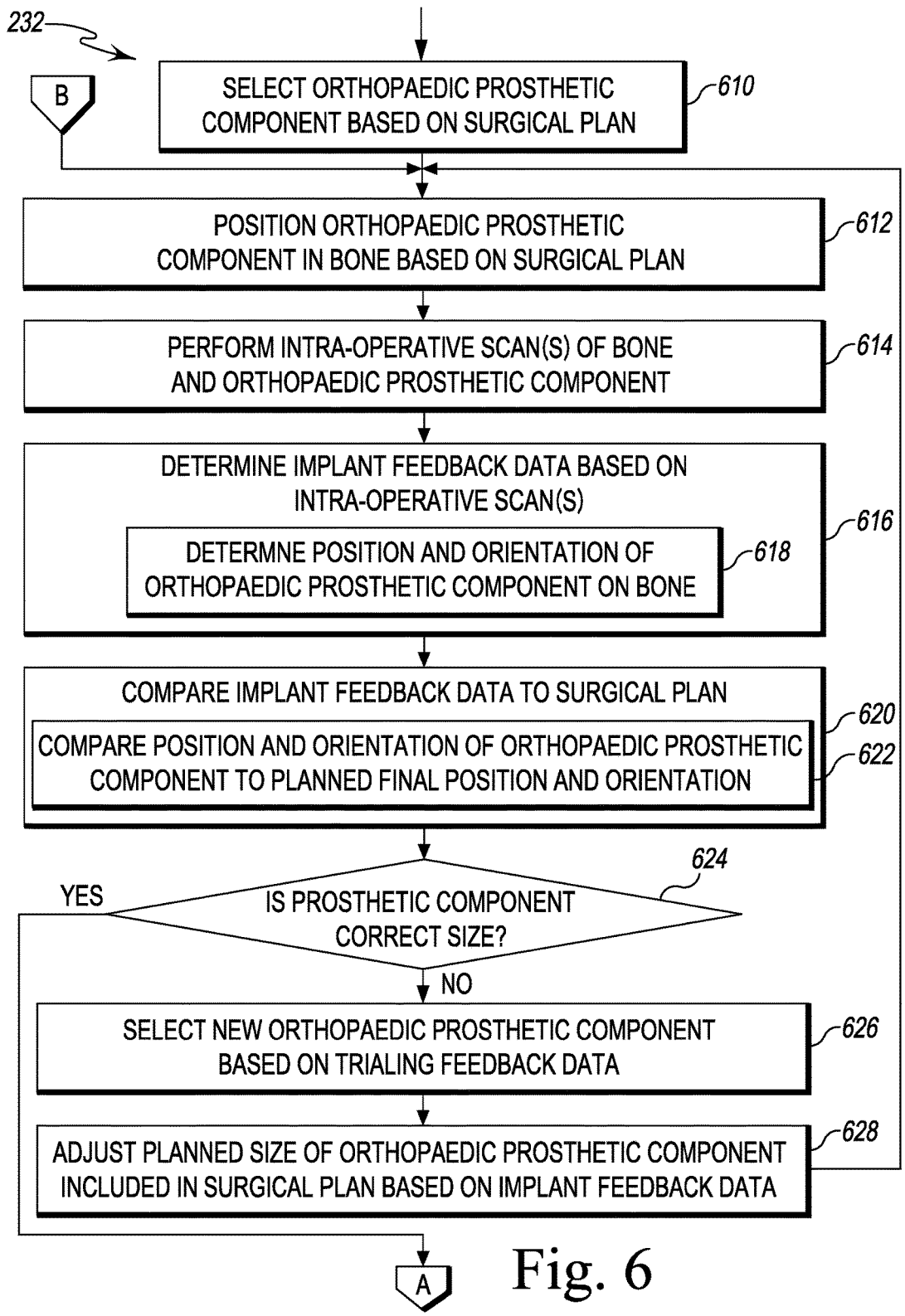
FIG. 6-7 are a simplified flow diagram for implanting an orthopaedic prosthetic component and confirming that the position and orientation of the orthopaedic prosthetic component matches the surgical plan.
Figure 7:
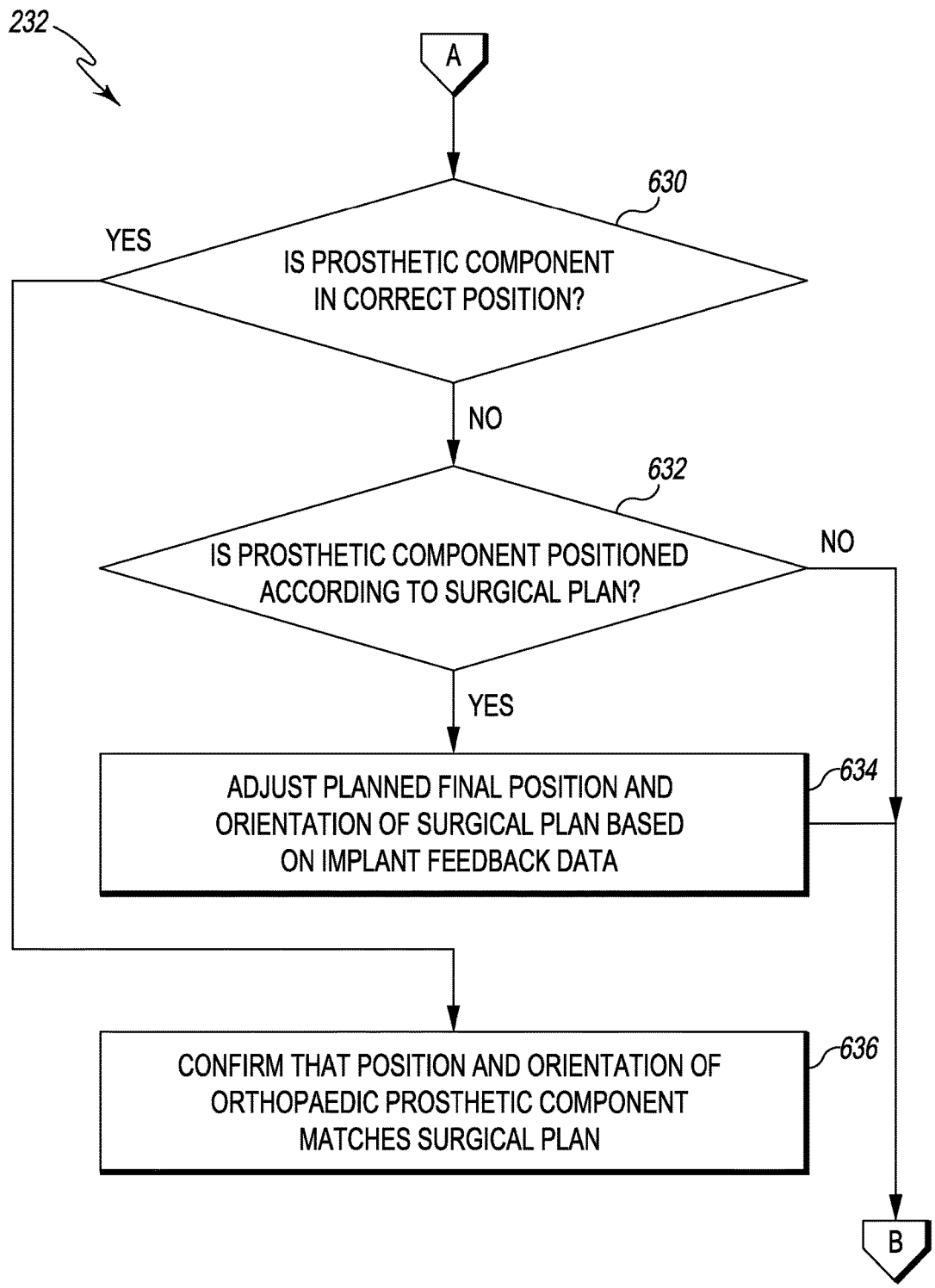

At block 232, the orthopaedic prosthetic component is implanted and one or more intra-operative scans of a final position and a final orientation of the orthopaedic prosthetic component in patient's body are performed. The one or more intra-operative scans are used to compare the planned final position and orientation of the orthopaedic prosthetic component to the actual final position and orientation of the orthopaedic prosthetic component. A more detailed description of block 232 is provided below and is shown in FIGS. 6-7.

Referring to FIG. 3, a method 228 for determining the position and orientation of the bone 810 of the patient 180 during the orthopaedic surgical procedure is shown. Before an orthopaedic surgical procedure, the surgical plan is generated, which includes the planned final position of the orthopaedic prosthetic component, the planned final orientation of the orthopaedic prosthetic component, and the planned implantation of angle of the orthopaedic prosthetic component. In general, the planned implantation angle is based on a planned orientation of the patient 180 during an orthopaedic surgical procedure and the planned final position and orientation of the orthopaedic prosthetic component in the patient 180. The actual position of the patient 180 in surgery may vary from the planned position of the patient 180 used to determine the planned implantation angle. If this is the case, the implanting the orthopaedic prosthetic component using the planned implantation angle will not result in the orthopaedic prosthetic component being in the planned final position and orientation.

Figure 8:
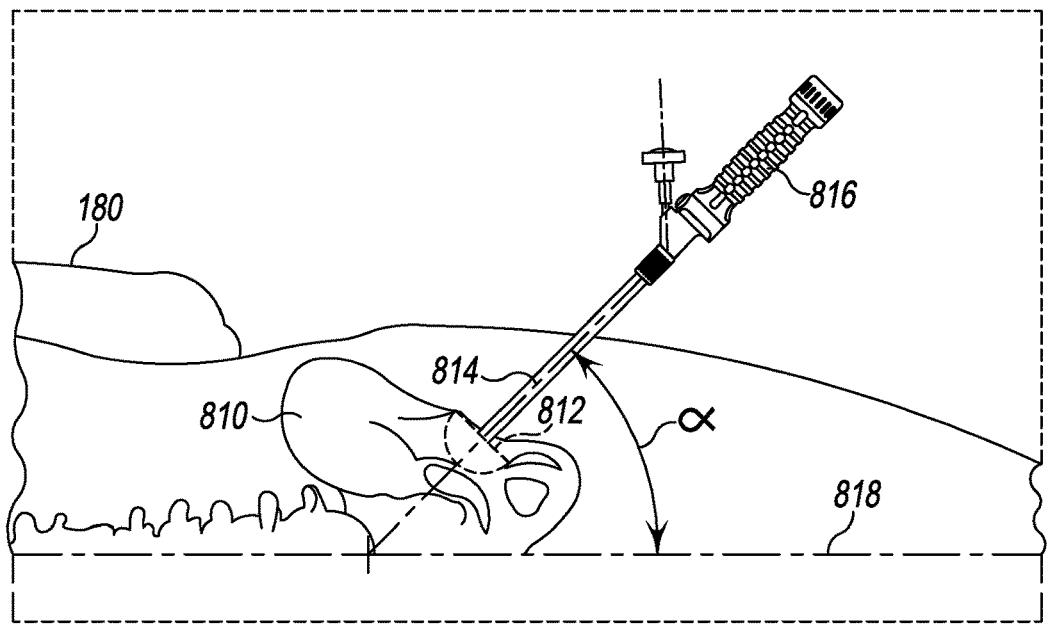
FIG. 8 is a plan view of a planned bone alignment of the patient and a planned implantation angle of the orthopaedic prosthetic component to be used during the orthopaedic surgical procedure of FIG. 1.

Referring now to FIG. 8, an image generated from data procured in a pre-operative scan shows a planned position and a planned orientation of a bone 810 of the patient 180 during an orthopaedic surgical procedure. In the illustrative embodiment, FIG. 8 depicts a planned position and orientation of a patient's coxal bone 810 during a hip arthroplasty. From the planned position and orientation of the patient's bone 810, a planned implantation angle $\alpha$ of the orthopaedic component 812 is determined and included in the surgical plan. In the illustrative embodiment, the planned implantation angle $\alpha$ is defined between an axis 814 defined by an implantation tool 816 and a reference plane 818. However, other references planes and/or methods of determining an implantation angle may be used. In some embodiments, the implantation tool 816 may use gravity to determine the implantation angle, and therefore the reference plane 818 may be the ground. In another embodiment, the reference plane 818 may be the surgical table.

Figure 9:
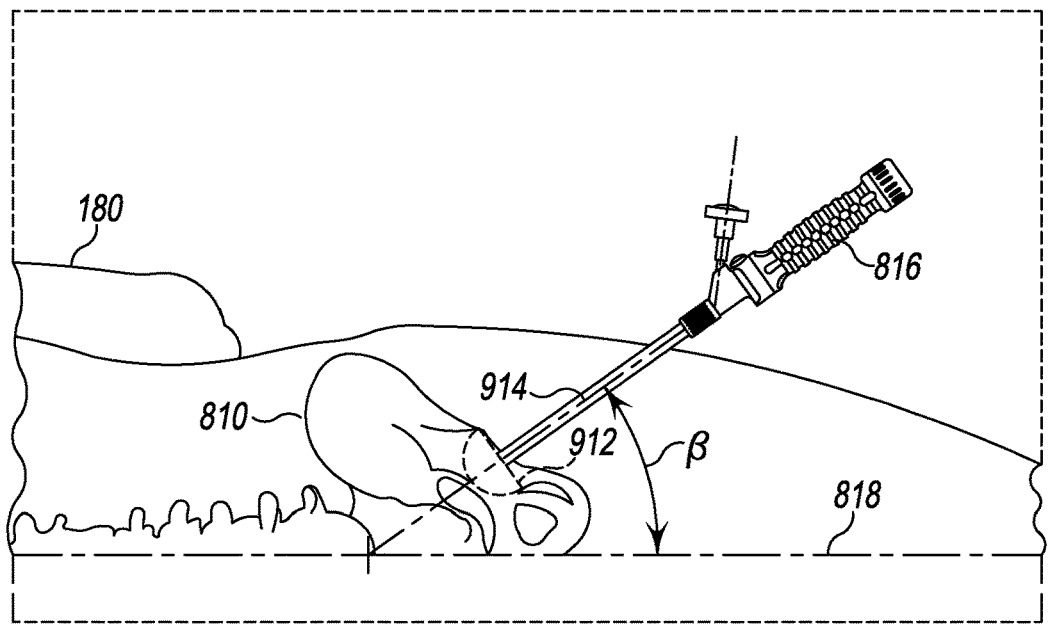
FIG. 9 is a plan view of an actual bone alignment of the patient and an adjusted implantation angle of the orthopaedic prosthetic component to be used during the orthopaedic surgical procedure of FIG. 1.

In contrast, FIG. 9 depicts an actual position and orientation of a coxal bone 810 of the patient 180 during the orthopaedic surgical procedure for implanting an orthopaedic component 912. While both FIGS. 8 and 9 show alignment of the coxal bone 810 of the patient 180, in other embodiments the position and orientation of other bones of the patient 180 may be determined (e.g., the femur of the patient 180).

To determine the actual position and orientation of the patient's bone 810, at block 310, one or more intra-operative alignment scans of the patient's bone 810 are performed using the hand-held device 110. To perform these intra-operative alignment scans, the hand-held device 110 may be inserted into the incision formed by the surgeon in the patient 180. The one or more intra-operative alignment scans are configured to produce alignment scan data of the surface of interest on the patient 180. In this example, the surface of interest is the exposed bone 810 of the patient 180 and the incision made in the patient 180. After the intra-operative alignment scans are performed, the hand-held device 110 is configured to transmit the scan data to the computing device 140 over the network 170. In the illustrative embodiment, network 170 is a wireless network and the hand-held device 110 transmits the scan data wirelessly to the computing device 140. In other embodiments, the network 170 may be a wired network. The computing device 140 may be configured to use the alignment scan data to generate one or more images, one or more three-dimensional models, or other data to output to a member of the surgical team.

In the illustrative embodiment, any of the intra-operative alignment scans described in this patent application are capable of being performed without moving the patient 180. For example, the hand-held device 110 may be operated in such a way that it is not necessary to move the patient 180 to a new location and it is not necessary to move the patient 180 relative to a reference plane when performing the intra-operative alignment scans. In this way, the intra-operative alignment scans are configured to provide data to the surgical team while minimally affecting the patient 180.

At block 312, bone alignment data is determined based on the intra-operative alignment scan, including determining the actual position and orientation of the bone 810 during the orthopaedic surgical procedure (block 314). As used in this application, "bone alignment data" refers to any data generated during surgery that indicates how a bone 810 of the patient 180 is positioned and oriented relative to a reference plane. Bone alignment data may be generated from the alignment scan data produced by the one or more intra-operative alignment scans, or data recorded by a member of the surgical team performing the orthopaedic surgical procedure. For example, bone alignment data may include one or more images generated from the intra-operative alignment scans, data generated by a member of the surgical team performing the orthopaedic surgical procedure, data generated by the computing device 140 (including three-dimensional models), or any other type of data that indicates the position and orientation of the bone 810 of the patient 180 during an orthopaedic surgical procedure.

As is shown in FIGS. 8 and 9, the actual position and orientation of the bone 810 of the patient 180 may vary from the planned position and orientation of the patient's bone 810 included in the surgical plan. At block 316, a member of the surgical team operates the computing device 140 to compare the bone alignment data to the surgical plan. If the bone alignment data does not match the surgical plan, at block 318, the surgical plan may be adjusted to reflect the actual position and orientation of the patient's bone 810.

If the actual position and orientation of the patient's body varies from the position and orientation used to prepare the surgical plan, at block 320, a member of the surgical team determines an adjusted implantation angle (e.g., implantation angle β in FIG. 9) based on the bone alignment data (e.g., actual position and orientation of the patient's bone 810). The surgical plan is adjusted to include the adjusted implantation angle β, where the implantation angle β is defined between an axis 914 defined by an implantation tool 816 and a reference plane 818.

In an embodiment, a member of the surgical team operates the computing device 140 to display bone alignment data and pre-operative data. Specifically, the one or more images generated from the intra-operative alignment scans may be superimposed on the one or more images generated from the pre-operative scans and displayed on the display 152 of the computing device 140. Upon viewing the superimposed images, a user of the surgical feedback system 100 may compare the planned position and orientation of the patient's bone 810 to the actual position and orientation of the patient's bone 810 and adjust the surgical plan according to that comparison.

Referring to FIGS. 4 and 5, a method 230 for performing a trialing procedure during the orthopaedic surgical procedure is shown. At block 410, a member of the surgical team selects an orthopaedic trialing component (see, for example, orthopaedic component 1010 in FIG. 10) based on the surgical plan. The orthopaedic trialing component is used as part of a trialing procedure to experimentally test the size, position, and orientation of a prosthetic component before implanting the orthopaedic prosthetic component. The orthopaedic trialing component is selected based on the planned size and planned type of the orthopaedic prosthetic component included in the surgical plan. In the illustrative embodiment, the orthopaedic trialing component is a reusable surgical instrument configured to mimic the size, shape, and functionality of a corresponding orthopaedic prosthetic component. In some embodiments, the surgical plan includes a trialing procedure that specifies which planned sizes of orthopaedic trialing components will be tested during the surgical procedure.

At block 412, a member of the surgical team positions the orthopaedic trialing component in the patient's bone 810 based on the planned final position and planned final orientation of the orthopaedic prosthetic component included in the surgical plan. At block 414, one or members of the surgical team perform one or more intra-operative trialing scans to determine a position and an orientation of the orthopaedic trialing component in the patient's exposed bone 810. In the illustrative embodiment, the intra-operative trialing scans are performed using the hand-held device 110 in such a way that the patient 180 is not moved or repositioned while the intra-operative trialing scans are performed. The intra-operative trialing scans are configured to generate trialing scan data of the surface of interest on the patient 180. In this example, the surface of interest is the patient's exposed bone 810 and the orthopaedic trialing component positioned thereon.

The trialing scan data generated by the intra-operative trialing scans is transmitted by the hand-held device 110 to the computing device 140 via the network 170. From the intra-operative trialing scans, the computing device 140 is configured to determine trialing feedback data indicative of the position and the orientation of the orthopaedic trialing component on the patient's bone 810 (blocks 416 and 418).

As used in this application, "trialing feedback data" refers to any data generated during a trialing process performed during the orthopaedic surgical procured. The trialing feedback data is generally indicative of the position and orientation of an orthopaedic trialing component on the bone 810 of a patient 180. For example, trialing feedback data may include one or more images generated by the computing device 140 from the trialing scan data, data generated by a member of the surgical team performing the orthopaedic surgical procedure, other data generated by the computing device 140 (including three-dimensional models), or any other type of data generated during the trialing process of an orthopaedic surgical procedure. It should be appreciated that trialing feedback data is not limited to data generated from the one or more intra-operative trialing scans.

At block 420, a member of the surgical team operates the computing device 140 to compare the trialing feedback data to the surgical plan including comparing the position and orientation of the orthopaedic trialing component to the planned final position and orientation included in the surgical plan (block 422). In the illustrative embodiment, the computing device 140 superimposes the images generated from the trialing scan data on images generated from the pre-operative scan data in the surgical plan showing the planned final position and orientation of the orthopaedic prosthetic component. The superimposed images are output to members of the surgical team via display 152.

Figure 10:
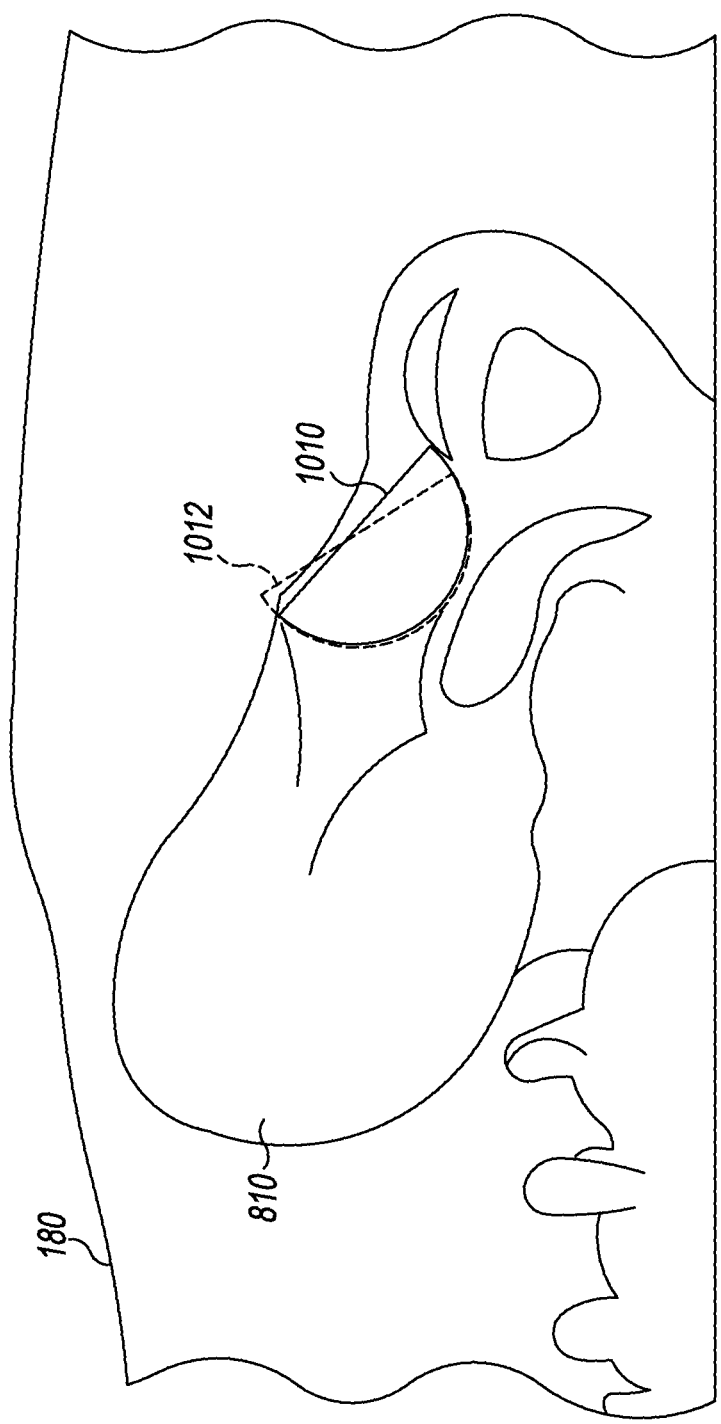
FIG. 10 is a plan view of the bone of the patient comparing the planned position and orientation of an orthopaedic component to the actual position and orientation of the orthopaedic component.

As shown in FIG. 10, the superimposed image output to the surgical team by the computing device 140 may include a depiction of the actual size, position, and orientation of the orthopaedic component 1010 and a depiction of a planned position and orientation of the orthopaedic component 1012 in the bone 810 of the patient 180. While FIG. 10 only shows one superimposed image, a plurality of superimposed images may be generated and output, where the plurality of superimposed images includes a plurality of views and perspectives of the surgical area. In some embodiments, the computing device 140 is configured to generate a three-dimensional model of the surgical region from data generated during the intra-operative trialing scans. The three-dimensional model is then compared to a three-dimensional model included in the surgical plan. The three dimensional model in the surgical plan may be generated based on pre-operative data, bone alignment data, and/or trialing feedback data previously generated.

At block 424, a member of the surgical team determines whether the orthopaedic trialing component is the correct size given the condition of the patient 180. Once an orthopaedic surgical procedure has begun a surgeon, or other surgical team member, may desire to adjust the surgical plan based on information determined during the orthopaedic surgical procedure. If a member of the surgical team determines that the orthopaedic trialing component is an incorrect size or type, at block 426, a new orthopaedic trialing component is selected to be used in another trialing process. At block 428, the surgical plan is adjusted to include an updated planned size of the orthopaedic prosthetic component based on the trialing feedback data.

If a member of the surgical team determines that the orthopaedic trialing component is the correct size and type, at block 430, a member of the surgical team operates the computing device 140 to determine whether the orthopaedic trialing component is positioned and oriented in such a way that the surgeon is satisfied that a similarly situated orthopaedic prosthetic component will meet the needs of the patient 180. Whether the position and orientation of the orthopaedic component will ultimately meet the needs of the patient 180 may be included in the trialing feedback data. Referring again to FIG. 10, the actual position and orientation of the orthopaedic component 1010 (trialing component or prosthetic component) may be compared to the planned position and orientation of the orthopaedic component 1012 by superimposing the images generated from the intra-operative trialing scans to images generated from the pre-operative data. The superimposed images are configured to provide a visual comparison between the planned and actual positions of the orthopaedic components 1010, 1012.

If the orthopaedic trialing component is not positioned correctly, at block 432, it is determined whether the position of the orthopaedic trialing component matches the position and orientation indicated in the surgical plan. If the member of the surgical team determines that the orthopaedic trialing component is positioned and oriented as indicated in the surgical plan, at block 434, the surgical plan is adjusted with a new planned final position and new planned final orientation based on this trialing feedback data. After the surgical plan has been adjusted, or if the orthopaedic trialing component is not positioned according to the surgical plan, the method 230 loops back to block 414 and the orthopaedic trialing component is repositioned to conform to the planned position and orientation of the orthopaedic prosthetic component included in the surgical plan.

If the orthopaedic trialing component is positioned correctly, at block 436, a member of the surgical team determines whether the trialing process is over. If the trialing process is not over, the member of the surgical team determines what adjustments are needed before performing the trialing process again. In the illustrative embodiment, the flow diagram shows the method 230 looping back to block 414, but it should be understood that the method 230 could loop back to any step based on the trialing feedback data based on the determinations made by the member of the surgical team using the surgical plan and the trialing feedback data.

Referring to FIGS. 6 and 7, a method 232 for implanting an orthopaedic prosthetic component and confirming that the position and orientation of the orthopaedic prosthetic component matches the surgical plan is shown. The method 232 for implanting an orthopaedic prosthetic component is similar to the method 230 for performing a trialing procedure discussed above.

At block 610, a member of the surgical team selects an orthopaedic prosthetic component (see, for example, orthopaedic component 1010 in FIG. 10) based on the surgical plan. The orthopaedic prosthetic component may be selected using pre-operative data, bone alignment data, trialing feedback data, or any combination thereof. Depending on the orthopaedic surgical procedure, a surgeon may not have collected all of the data listed above. For example, the orthopaedic prosthetic component might be selected only using pre-operative data and bone alignment data.

At block 612, the orthopaedic prosthetic component is positioned in the exposed bone 810 of the patient 180 is preparation to implant the orthopaedic prosthetic component permanently in the patient 180. At block 614, one or more intra-operative scans are are performed of the exposed bone 810 and the orthopaedic prosthetic component and implant feedback data is generated. As used in this application, "implant feedback data" refers to any data generated while implanting the orthopaedic prosthetic component in the patient 180 during the orthopaedic surgical procedure. The implant feedback data is indicative of the position and orientation of an orthopaedic prosthetic component on the bone 810 of a patient 180 (see block 616). For example, implant feedback data may include implant scan data generated by the intra-operative implant scans, data generated by a member of the surgical team performing the orthopaedic surgical procedure, data generated by the computing device 140 (including images or three-dimensional models), or any other type of data generated during the implantation process of the orthopaedic prosthetic component during an orthopaedic surgical procedure.

At block 620, a member of the surgical team operates the computing device 140 to compare the implant feedback data to the surgical plan including comparing the position and orientation of the orthopaedic prosthetic component to the planned final position and orientation included in the surgical plan (block 622). At block 624, a member of the surgical team determines whether the orthopaedic prosthetic component is sized to meet the needs of the patient. For example, a surgeon may determine whether the orthopaedic prosthetic component will allow the patient 180 the desired amount of movement, stability, and comfort.

If the member of the surgical team determines the orthopaedic prosthetic component is sized incorrectly, a new orthopaedic prosthetic component is selected based on the implant feedback data (see block 626). Additionally, the surgical plan is also updated with the implant feedback data and the new planned size of orthopaedic implant (see block 628).

At block 630, a member of the surgical team determines whether the orthopaedic prosthetic component is positioned correctly based on the implant feedback data. At block 632, a member of the surgical team determines whether the orthopaedic prosthetic component is positioned according to the surgical plan. If the orthopaedic prosthetic component is not positioned to meet the needs of the patient 180 and is not positioned according to the surgical plan, the position and orientation of the orthopaedic prosthetic component is adjusted to conform to the planned position and orientation included in the surgical plan. If the orthopaedic prosthetic component is not positioned to meet the needs of the patient 180 and is positioned according to the surgical plan, the planned final position and orientation of the orthopaedic prosthetic component is adjusted based on the implant feedback data (see block 634).

At block 636, a member of the surgical team uses the implant feedback data to confirm that the orthopaedic prosthetic component is implanted according to the surgical plan. Once the surgeon on the surgical team is satisfied that the orthopaedic prosthetic component is sized, positioned, and oriented correctly, the orthopaedic prosthetic component is fixed in place relative to the bone 810 of the patient 180, the full prosthetic is assembled, and the orthopaedic surgical procedure is moved towards completion.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A surgical feedback system comprising:
a hand-held device configured to obtain a second scan of a patient's bone, the second scan including a position and an orientation of an orthopaedic prosthetic component implanted in the patient's bone, and
a computing device communicatively coupled to the hand-held device, the computing device configured to:
receive data from a first scan of the patient's bone,
compare a position and an orientation of the patient's bone included in the data from the first scan to a planned position and a planned orientation of the patient's bone in a surgical plan,
generate an adjusted planned position and an adjusted planned orientation of the orthopaedic prosthetic component relative to the patient's bone based on the comparison of the position and the orientation of the patient's bone included in the data from the first scan to the planned position and the planned orientation of the patient's bone in the surgical plan,
receive data from the second scan of the patient's bone by the hand-held device, and
confirm that the position and the orientation of the orthopaedic prosthetic component included in the data from the second scan matches the adjusted planned position and the adjusted planned orientation of the orthopaedic prosthetic component.

2. The surgical feedback system of claim 1, wherein the hand-held device comprises an optical detector configured to detect electromagnetic radiation reflected from a surface of interest on the patient.

3. The surgical feedback system of claim 2, wherein the optical detector is configured to be positioned inside of an incision formed in the patient's tissue.

4. The surgical feedback system of claim 2, wherein the hand-held device is a white light scanner configured to determine one or more locations of the surface of interest on the patient by detecting one or more characteristics of white light reflected from the surface of interest.

5. The surgical feedback system of claim 2, wherein the hand-held device is a laser scanner configured to determine one or more locations on the surface of interest on the patient by detecting one or more characteristics of laser light reflected from the surface of interest.

6. The surgical feedback system of claim 1, wherein the computing device is communicatively coupled to the hand-held device via a network.

7. The surgical feedback system of claim 1, wherein the computing device is further configured to display a comparison of the position and the orientation of the patient's bone included in the data from the first scan to the planned position and the planned orientation of the patient's bone in the surgical plan.

8. The surgical feedback system of claim 1, wherein the computing device is further configured to display a comparison of the position and orientation of the orthopaedic prosthetic component included in the data from the second scan to a planned component position and a planned component orientation of the orthopaedic prosthetic component in the surgical plan.

9. The surgical feedback system of claim 1, wherein:
the hand-held device is further configured to obtain a third scan of an orthopaedic trialing component in the patient's bone, the third scan including a first position and a first orientation of the orthopaedic trialing component, and
the computing device is further configured to determine trialing feedback data by comparing the first position and the first orientation of the orthopaedic trialing component included in data from the third scan to a planned component position and a planned component orientation of the orthopaedic prosthetic component in the surgical plan.

10. The surgical feedback system of claim 9, wherein:
the hand-held device is further configured to obtain a fourth scan of the orthopaedic trialing component in the patient's bone, the fourth scan including a second position and a second orientation of the orthopaedic trialing component, and
the computing device is further configured to determine additional trialing feedback data by comparing the second position and the second orientation of the orthopaedic trialing component included in data from the fourth scan to the planned component position and the planned component orientation of the orthopaedic prosthetic component in the surgical plan.

11. The surgical feedback system of claim 9, wherein:
the hand-held device is further configured to obtain a fourth scan of a different orthopaedic trialing component in the patient's bone, the fourth scan including a second position and a second orientation of the different orthopaedic trialing component, and
the computing device is further configured to determine additional trialing feedback data by comparing the second position and the second orientation of the different orthopaedic trialing component included in data from the fourth scan to the planned component position and the planned component orientation of the orthopaedic prosthetic component in the surgical plan.

12. A surgical feedback system comprising:

a hand-held device configured to obtain a second scan of a patient's bone, the second scan including a first position and a first orientation of an orthopaedic trialing component positioned in the patient's bone, and a computing device communicatively coupled to the hand-held device, the computing device configured to:

receive data from a first scan of the patient's bone, compare a position and an orientation of the patient's bone included in the data from the first scan to a planned position and a planned orientation of the patient's bone in a surgical plan, generate an adjusted planned position and an adjusted planned orientation of an orthopaedic prosthetic component relative to the patient's bone based on the comparison of the position and the orientation of the patient's bone included in the data from the first scan to the planned position and the planned orientation of the patient's bone in the surgical plan, receive data from the second scan of the patient's bone by the hand-held device, and determine trialing feedback data by comparing the first position and the first orientation of the orthopaedic trialing component included in the data from the second scan to the adjusted planned position and the adjusted planned orientation of the orthopaedic prosthetic component relative to the patient's bone.

13. The surgical feedback system of claim 12, wherein:

the hand-held device is further configured to obtain a third scan of the orthopaedic trialing component in the patient's bone, the third scan including a second position and a second orientation of the orthopaedic trialing component, and the computing device is further configured to determine additional trialing feedback data by comparing the second position and the second orientation of the orthopaedic trialing component included in data from the third scan to the adjusted planned position and the adjusted planned orientation of the orthopaedic prosthetic component relative to the patient's bone.

14. The surgical feedback system of claim 12, wherein:

the hand-held device is further configured to obtain a third scan of a different orthopaedic trialing component in the patient's bone, the third scan including a second position and a second orientation of the different orthopaedic trialing component, and the computing device is further configured to determine additional trialing feedback data by comparing the second position and the second orientation of the different orthopaedic trialing component included in data from the third scan to the adjusted planned position and the adjusted planned orientation of the orthopaedic prosthetic component relative to the patient's bone.

15. The surgical feedback system of claim 12, wherein:

the hand-held device is further configured to obtain a third scan of the orthopaedic prosthetic component implanted in the patient's bone, the third scan including a position and an orientation of the orthopaedic prosthetic component, and the computing device is further configured to receive data from the third scan of the patient's bone by the hand-held device and to confirm that the position and the orientation of the orthopaedic prosthetic component included in the data from the third scan matches the adjusted planned position and the adjusted planned orientation of the orthopaedic prosthetic component.

16. The surgical feedback system of claim 12, wherein the computing device is further configured to display the trialing feedback data.

17. The surgical feedback system of claim 12, wherein the computing device is communicatively coupled to the hand-held device via a network.

18. A surgical feedback system comprising:

a hand-held device configured to obtain (i) a first scan of a patient's bone, the first scan including a first position and a first orientation of an orthopaedic trialing component positioned in the patient's bone, and (ii) a second scan of the patient's bone, the second scan including a position and an orientation of an orthopaedic prosthetic component implanted in the patient's bone, and a computing device communicatively coupled to the hand-held device, the computing device configured to:

receive data from the first scan of the patient's bone by the hand-held device, and determine trialing feedback data by comparing the first position and the first orientation of the orthopaedic trialing component included in the data from the first scan to a surgical plan, output an adjusted position and an adjusted orientation for implantation of the orthopaedic prosthetic component based on the trialing feedback data, receive data from the second scan of the patient's bone by the hand-held device, and confirm that the position and the orientation of the orthopaedic prosthetic component included in the data from the second scan matches the adjusted position and the adjusted orientation for the orthopaedic prosthetic component.

19. The surgical feedback system of claim 18, wherein the adjusted position and the adjusted orientation output based on the trialing feedback data are different than a planned position and a planned orientation for implantation of the orthopaedic prosthetic component included in the surgical plan.

20. The surgical feedback system of claim 18, wherein the computing device is communicatively coupled to the hand-held device via a network.

* * * * *